(12) United States Patent
Glahn

(10) Patent No.: US 6,207,194 B1
(45) Date of Patent: Mar. 27, 2001

(54) PECTIN PROCESS AND COMPOSITION

(75) Inventor: Poul-Egede Glahn, Skensved (DK)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 08/890,983

(22) Filed: Jul. 10, 1997

Related U.S. Application Data

(63) Continuation of application No. 08/161,634, filed on Dec. 2, 1993.

(51) Int. Cl.[7] .................................................. A61K 9/14
(52) U.S. Cl. .................. 424/489; 424/401; 424/439; 424/70.2; 424/443; 424/65; 424/49; 424/484; 424/499
(58) Field of Search .................... 424/401, 489, 424/443, 439, 499

(56) References Cited

U.S. PATENT DOCUMENTS

| | | |
|---|---|---|
| 2,132,577 | 2/1938 | Olsen . |
| 3,396,034 | 8/1968 | Blondheim . |
| 3,946,110 | 3/1976 | Hill . |
| 4,268,533 | 5/1981 | Williams . |
| 4,686,106 | 8/1987 | Ehrlich . |
| 4,774,095 | 9/1988 | Kleinschmidt et al. . |
| 4,800,096 | 1/1989 | Digiovaccino . |
| 4,911,946 | 3/1990 | Singer et al. . |
| 5,324,531 | 6/1994 | Hoefler . |

FOREIGN PATENT DOCUMENTS

| | | |
|---|---|---|
| 2442980 | 3/1976 | (DE) . |
| 432835A1 | 6/1991 | (EP) . |
| 0432835 | 3/1994 | (EP) . |
| 432835B1 | 3/1994 | (EP) . |
| 1185280 | 7/1959 | (FR) . |
| 1474990 | 9/1974 | (GB) . |
| 60-110270 | 6/1985 | (JP) . |
| 8912648 | 12/1989 | (WO) . |

OTHER PUBLICATIONS

Derwent Publications Ltd., London, GB, Week 8430, AN 84–187728 & SU–A–1 056 990, Nov. 30, 1993– Abstract.

Derwent Publications Ltd., London, GB, Week 8530, AN85–181395 & JP–A–60 110270, Jun. 15. 1995– Abstract.

Portion of English Language Translation (pp. 4–6) of Oppostion of Copenhagen Pectin to Petition of P.E. Glahn for Legal Aid Submitted Sep. 7, 1996.

*Primary Examiner*—Thurman K. Page
*Assistant Examiner*—Liliana Di Nola-Baron
(74) *Attorney, Agent, or Firm*—Greenblum & Bernstein, P.L.C.

(57) ABSTRACT

A composition comprising a dry cationic pectin salt which when suspended in water swells to heat stable particles having a mean equivalent diameter greater than 100 micrometers. Food, cosmetic, superabsorbent and skin adhesive compositions containing the dry cationic pectin salt. A process for making the dry cationic pectin salt having the steps: a) converting a pectin starting material into a pectinate in a liquid medium, b) drying the pectinate, and c) selecting conditions in steps (a) and/or (b) that allow for the production of pectinate which when suspended in water swells to heat stable particles having a mean equivalent diameter greater than 100 micrometers.

21 Claims, No Drawings

PECTIN PROCESS AND COMPOSITION

This application is a continuation, of application Ser. No. 08/161,634, filed Dec. 02, 1993, pending.

The present invention relates to pectin compositions, processes for preparing the same, and the use of the said pectin compositions.

BACKGROUND OF THE INVENTION

Processes for preparation of pectins are well known, as are many uses for these products. In general, typical pectin processes include the steps of:

(1) acid extraction from plant starting material at low pH,
(2) purification of the liquid extract, and
(3) isolation of the extracted pectin from the liquid.

In the acid extraction step, plant material is typically treated with dilute acids such as nitric-, sulfuric-, hydrochloric- or other inorganic or organic acids to remove the pectin from the cellulose components of the material. Commonly used plant starting materials are citrus peels from juice production and apple pomace from apple juice and cider production. Other plant starting materials can also be used, such as sugar beet, before or after sugar extraction, sunflower heads after removal of the seed, and other vegetables or waste products from plants. Extraction conditions are selected such that a major part of the pectin molecules contained in the plant starting material is transferred from the cell walls of said plant starting material to the extraction medium The quantity and quality of the extracted pectin depends on the raw material source and the selection and control of the extraction conditions such as pH, temperature and extraction time.

ASfter the acid extraction step, a mixture of solid plant material and liquid that contains the pectin remains. This mixture is then subjected to a purification step in which the solid plant material is removed by filtration, centrifugation or other conventional separation steps known to those skilled in the art.

The extract can, optionally, be further purified by ion exchange and concentrated by evaporation of part of the water. Alternatively, the purification steps can be carried out by reverse osmosis, concentrating and purifying the extract in the same steps.

The pectin in the acid extract can be isolated by reacting with aluminum salts after adjusting the pH. The aluminum pectin gel thus formed is treated with alcohol/acid mixture to wash out the aluminum salt and transform the pectin into pectic acid. The pectic acid can then be neutralized and dried by washing with slightly alkaline alcohol.

More commonly, the pectin is isolated by treating the pectin solution with an appropriate alcohol to render the pectin insoluble in the ensuing blend of alcohol and water. Any alcohol or other organic solvent miscible with water can be used, most often ethyl alcohol, methyl alcohol or isopropyl alcohol, isopropyl alcohol is most preferred.

The insolubilized pectin is separated from the alcohol/water mixture by appropriate means such as filtration, centrifugation, etc. The resulting pectin cake is dried and milled to the desired particle size.

In typical commercial processes, the presence of high levels of polyvalent cation is avoided in steps (1) and (2) as described above. While low levels of cation, i.e., those levels naturally present in the starting material, may be tolerated in some instances. It has been the general practice to never add additional cation(s) to the processes. This would result in unacceptable increases in viscosity and unacceptable levels of insoluble pectin in the final product.

Industrially produced pectins are made up primarily of anhydrogalacturonic acid chains in which rhamnose may be found. Neutral sugars may be attached to the rhamnose units. The anhydrogalacturonic acid makes up at least 65% of the dry matter in commercial type pectins. The galacturonic acids are partly esterified with methyl alcohol.

According to convention, pectins with more than 50% of the carboxylic acids groups esterified with methyl alcohol are referred to as high methoxyl pectins; whereas, pectins with less than 50% of the carboxylic acid groups esterified with methyl alcohol are called low methoxyl pectins.

The extract as obtained by the commercial production is composed of those molecules that are soluble under the conditions of pH, temperature, and time used during the extraction. The extract is composed of a mixture of molecules which differ according to molecular weight, distribution of molecular weight, and degree of esterification.

The properties of the pectin obtained are, therefore, very much dependent of the specific mixture of molecular configurations present in the isolated pectin. This mixture of molecules can be controlled only to a certain degree by the pectin manufacturer by selection of raw materials and extraction conditions. For this reasons, variation in pectin properties is seen from extract to extract, from manufacturer to manufacturer, and normalization of the properties is generally necessary. This may be accomplished by blending different extracts and diluting with acceptable diluent such as sugar, dextrose, fructose, etc.

One of the main functional variations between high methoxyl pectins is their sensitivity to the presence of varying concentrations of polyvalent cations. It is known that pectins of high degree of esterification, e.g., greater than fifty, are not particularly useful for applications involving reaction of the pectin with polyvalent cations such as calcium.

European patent application 0432,835 describes the production of a cation salt of pectin in the form of microgels. In said patent, a solution of pectin is reacted with a solution of a di- or trivalent metal salt, preferably calcium salts, under high shear conditions to create calcium pectin microgels with a mean equivalent diameter not exceeding 100 micrometers, more preferably not exceeding 50 micrometers. These microgels are described as being used as fat substitutes among other things.

U.S. Pat. No. 4,911,945 discloses a fat substitute of carbohydrate particles that display a fat-like mouthteel characteristic when the particles have a substantially spheroidal shape and a mean diameter distribution in the range of 0.1 about 2 microns with less than about 2% of the total particles being over 3 microns. The carbohydrates includes starches, gums, and cellulose and can be reacted with a calcium ion to form micro-colloid particles of the invention.

The above discussed references are seen to express a strong preference for the use of small particles for the successful simulation of fat in foods.

SUMMARY OF INVENTION

It has unexpectedly been discovered that fat simulating compositions can be achieved using certain pectin gels having large particles sizes. These gels also have beneficial properties in other applications such as cosmetics.

Accordingly, the present invention relates to a food composition comprising in admixture of foodstuff and dry cationic pectin salt which, when suspended in distilled water, will swell to heat stable particles having a mean equivalent diameter of greater than 100 micrometers.

The present invention further relates to a cosmetic composition comprising in admixture a cosmetic starting material and dry cationic pectin salt which, when suspended in distilled water, will swell to heat stable particles, having a mean equivalent diameter greater than 100 micrometers.

The present invention further relates to a superabsorbent composition comprising in combination superabsorbents carrier and a dry cationic pectin salt which, when suspended in distilled water, will swell to heat stable particles having a mean equivalent diameter greater than 100 micrometers.

The present invention also relates to a skin adhesive composition comprising in admixture skin adhesive starting material and a dry cationic pectin salt which, when suspended in distilled water will swell to heat stable particles, having a mean equivalent diameter greater than 100 micrometers.

In addition, the present invention relates to a composition comprising a dry cationic pectinate salt, which when suspended in distilled water, will swell to heat stable particles having a mean equivalent diameter greater than 100 micrometers.

The present invention further relates to a process for making the pectinate described above comprising (a) converting a pectin starting material into a pectinate in a liquid medium, (b) drying the pectinate, and (c) selecting the conditions in steps (a) and/or (b) such as to allow for the production of dry pectinate which, when suspended in distilled water will swell to heat stable particles having a mean equivalent diameter greater than 100 micrometers.

DETAILED DESCRIPTION OF THE INVENTION

As indicated above, the present invention relates to a food composition comprising in admixture a foodstuff and dry cationic pectin salt which, when suspended in distilled water, will swell to heat stable particles having a mean equivalent diameter of greater than 100 micrometers. The equivalent diameter distribution of the particles can suitably be determined by microscopical images. Although such may be done by means of an image analyzing computer, it is preferred to determine the diameter distribution by hand. A proper magnification should be chosen for determining diameter distribution. A magnification of 20–40X would be appropriate for determining particle sizes in accordance with the present invention.

What is intended by the term "heat stable" is that upon heating a suspension of pectin production in distilled water, the suspended particles will not dissolve. This property can be determined by first suspending 2 weight percent of the pectinate production in distilled water at 25° C. of pH of 4 and slowly heating the suspension to 90° C. within about 10 minutes. The pectinate product is heat stable in accordance with the present invention if after completion of heating of the pectinate product, the suspended particles are still visible to the naked eye.

The foodstuff used in accordance with the present invention could be dry or wet. In connection with the dry cationic pectin salt, the term "dry" is intended to include both the admixture of dry pectin powder or the admixture of pre-mixed dry pectin powder and liquid with the foodstuff.

"Mean equivalent diameter" means number weighted mean equivalent diameter.

In accordance with the present invention, the pectinate composition can be prepared by the process of converting a pectin starting material into a pectinate in a liquid medium, drying the pectinate and selecting the conditions in one of the above mentioned steps such as to allow for the production of dry pectinate which, when suspended in distilled water, will swell to heat stable particles having a mean equivalent diameter greater than 100 micrometers. This process is performed under non-sheet (or laminar flow) conditions.

As indicated, compositions in accordance with the present invention comprise dry cationic pectin salt. Such pectin can be obtained by the treatment of pectin starting material obtained by the acid extraction of plant material. The pectin starting material could be the acid pectin extract after purification or it could be wet pectin cake obtained after treating the acid pectin solution with an alcohol. Further, the pectin starting material could be the dried or partly dried pectin in said pectin cake from the precipitation, or it could be the dried, milled pectin powder as normally produced by pectin manufacturers. In the event that dried or partly dried pectin is used, it is mixed with alcohol/water to partially solubilize the pectin.

The pectin starting material is treated with a cation-containing preparation. As used herein, "cation-containing preparation" is intended to mean any source of free cation. The cation is preferably a metal ion derived from salts selected from the group consisting of alkaline earth metal salts, alkali metal salts, transition metal salts, and mixtures thereof, provided that such salts are reasonably soluble in the solvent, e.g., water or water/alcohol mixtures. The preferred salts are salts of calcium, magnesium, zinc, or iron. When a metal ion is used as the cation, it is preferably selected from the group consisting of calcium, iron, magnesium, zinc, potassium, sodium, aluminum, and manganese, and mixtures thereof. More preferably, the metal cations are selected from the group consisting of calcium, iron, zinc, and magnesium. Most preferably, the cation is calcium. Mixtures of two or more metal cations may be employed. However, if a monovalent metal cation is employed, a di- or trivalent metal cations, such as calcium, must also be present. Preferably, when such mixtures are used, one of the metal cations is calcium.

Examples of metal salts that can be used in the practice of the present invention, provided they are reasonably soluble in the solvent, include, but are not limited to, calcium acetate, calcium acid phosphate, calcium carbonate, calcium chloride, calcium citrate, calcium dihydrogen phosphate, calcium formate, calcium gluconate, calcium glutamate, calcium glycerate, calcium glycerophosphate, calcium glycinate, calcium hydrogen phosphate, calcium hydroxide, calcium iodide, calcium lactate, calcium lactophosphate, calcium magnesium carbonate, calcium magnesium inositol hexaphosphate, calcium phosphate tribasic, calcium-o-phosphate, calcium proplonate, calcium pyrophosphate, calcium succinate, calcium sucrate, calcium sulfite, calcium tetraphosphate, iron (II) acetate, iron (III) acetate, iron (III) acetate hydroxide, iron (III) ammonium chloride, iron (III) ammonium citrate, iron (II) ammonium sulfate. iron (II) carbonate, iron (II) chloride, iron (III) chloride, iron choline citrate, iron (II) citrate, iron dextran, iron (II) formate, iron (III) formate, iron (III) hypophosphite, iron (II) lactate, iron (II) acetate, iron (II) phosphate, iron (III) potassium oxalate, iron (III) pyrophosphate, iron (III) sodium citrate, iron (III) sodium pyrophosphate, iron (II) sulfate, iron (III) sulfate, magnesium ammonium phosphate, magnesium ammonium sulfate, magnesium carbonate, magnesium chloride, magnesium citrate, magnesium dihydrogen phosphate, magnesium formate, magnesium hydrogen phosphate, magnesium hydrogen-o-phosphate, magnesium hydroxide, magnesium hydroxide carbonate, magnesium lactate, magnesium nitrate, magnesium oxalate, magnesium oxide, magnesium phosphate, magnesium propionate, magnesium pyrophosphate, magnesium sulfate, zinc acetate, zinc ammonium sulfate, zinc carbonate, zinc chloride, zinc citrate, zinc formate, zinc hydrogen phosphate, zinc hydroxide, zinc lactate, zinc nitrate, zinc oxide, zinc phosphate, zinc phosphate monobasic, zinc phosphate tribasic, zinc-o-phosphate, zinc propionate, zinc pyrophosphate, zinc sulfate, zinc tartrate, zinc valerate, and zinc-iso-valerate.

The preferred salts are calcium salts such as calcium chloride, calcium hydroxide, calcium acetate, calcium propionate, calcium oxide, calcium gluconate, calcium lactate, and calcium carbonate, The most preferred calcium salt is calcium chloride.

Preferably, the cation-containing preparation contains a di- or trivalent cation, and optionally at least one water miscible solvent. Under appropriate conditions, the polyvalent salt forms an insoluble calcium pectin salt or gel. The preferred cation is calcium ion in aqueous solution, optionally mixed with a solvent such as methyl alcohol, ethyl alcohol, propyl alcohol, isopropyl alcohol, acetone ethyl acetate, and any other organic solvent that is miscible with water. When mixed with alcohol, care should be exercised to avoid alcohol levels that will results in precipitation of the pectin and make the cation compound insoluble. The preferred solution is a mixture of alcohol and water. Most preferred is a mixture of isopropyl alcohol and water.

Blends of mono-, di-, and trivalent salts may also be used. Preferred are blends of potassium or sodium with calcium salts.

The cations concentration can be varied over a wide range, with the upper limit being determined only by economic and practical considerations. It is preferred that the upper limit be about 60 nM cations per liter of reaction medium A more preferred upper limit is about 45 mM cation per liter of reaction medium. The preferred lower limit is about 5 mM cation per liter of reaction medium. A more preferred lower limit is about 10 mM cation per liter of reaction medium, with about 30 mM being the most preferred lower limit.

The pH of the reaction medium influences the ability of the pectin starting material to form a cationic salt. If the pH is too low, no cationic salt is formed. It is believed that the pH should be at least about 2. The lower limit is preferably at least about 3, with about 4 being the most preferred. The upper limit of the pH is only determined by the stability of the pectin starting material under the combination of pH, temperature, and time being used. It is believed that the upper limit should be about 8. The preferred upper limit should be about 6, with about 5 being the most preferred upper limit.

The purified pectin extract is reacted with a solution of cationic salt, preferably calcium salt, under non-shear flow conditions, forming a reaction mixture that contains large gel particles visible to the naked eye.

The resulting reaction mixture is then dehydrated, dried and milled. The dehydration is performed to remove the bulk of the water before the drying step. While any known technique could be used for dehydration, preferably the reaction mixture is treated with alcohol. The water/alcohol phase formed in the dehydration is substantially removed by decantation, centrifugation or filtration using any conventional technique. Drying is accomplished by conventional techniques, e.g., atmospheric or reduced-pressure ovens, to a moisture content of less than 50%, preferably less than 25%. The drying temperature should be maintained below the temperature at which the pectin starts to lose its properties, e.g., color, molecular weight, etc. Milling techniques are well-known and any known technique can be used to mill the pectin product to the desired particle size. It is most preferred that the final product be in dry, powder form, with a moisture content of 12% or less. Dry, powdered form is intended to mean that the product be pourable without substantial caking. This is preferred for ease of use.

Alternatively, pectinate compositions in accordance with the present invention can be made by dissolving the metal salts into a hot pectin solution as produced by the pectin manufacturing process or by dissolving already prepared pectins in hot water and adding the metal salts to the pectin solution. The pectin solution can then be dried in ways known to those skilled in the art, e.g., by mixing the pectin metal salt solution with an organic solvent miscible with water. The insolubilized metal pectinate is then dried directly or it can be washed to eliminate non-reacted metal salt.

Alternatively, the metal salt can be formed by reacting the precipitated pectin with a solution of metal salt under appropriate conditions of pH transforming the precipitated pectin into the desired salt form.

Alternatively, the salt of pectinate can also be formed by ion exchange of the dried pectin suspended in a water miscible organic liquid in which the desired metal salt is dissolved, and in this way exchanging the ions with the partly swollen pectin particles.

Processes used to make the dry cationic pectin salt in accordance with the present invention could be either continuous or batchwise, with continuous being preferred.

The dry cationic pectin salt in accordance with the present invention is one which, when suspended in distilled water, will swell to a mean equivalent diameter size of greater than 100 micrometers. Preferably the mean equivalent diameter is at least 150 micrometers, more preferably at least 200 micrometers. Even more preferred is a mean equivalent diameter of at least 300 micrometers. It is most preferred that the particle size is at least 400 micrometers.

Preferably, more than 90%, more preferably, more than 95% by weight of the particles have an equivalent diameter greater than 200 micrometers, preferably at least 300 micrometers, more preferably at least 400 micrometers.

Also in accordance with the present invention, a food composition comprises in admixture a foodstuff and the pectin compositions described above. As used herein, foodstuff is intended to mean any food, food compositions, food ingredient, or food product, whether comprised of a single ingredient or a mixture of two or more ingredients, whether liquid, liquid containing, or solid, whether primarily carbohydrate, fat, protein, or any mixture thereof, whether edible per se or requiring preliminary conventional steps like cooking, mixing, cooling, mechanical treatment, and the like.

The invention is particularly applicable to meat, poultry, fish products, dairy products such as milk, ice cream, yoghurt, cheese, pudding, and flavored dairy drinks, baked foods such as bread, cake, cookies, crackers, biscuits, pies, donuts, pretzels, and potato chips, non-diary spreads, mayonnaise, soups, sauces, dips, dressings, frozen confections, fruit preparations, jams and jellies, beverages, water gels, confectionary jelly, and low fat spreads.

Further in accordance with the present invention, a personal hygienic device contains the pectins compositions as described above. The invention is particularly applicable to tampons, incontinent devices, disposable diapers, and would dressings.

Additionally, in accordance with the present invention, cosmetic composition comprises at least one cosmetic ingredient and the pectin compositions as described above. The composition is especially applicable to sun tan lotions, sun screen compositions, creams which include emollients such as isopropylmyristate, silicone oils, mineral oils, and vegetable oils which give rise to a tactile response in the form of an increase in skin lubricity, and skin coolants such as menthol, menthyl lactate, menthyl pyrrolidone carboxylate N-ethyl-p-menthane-3-carboxamide and other derivatives of menthol, all of which give rise to a tactile response in the form of a cooling sensation on the skin, perfumes, deodorants other than perfumes, whose functions is to reduce the level of, or eliminate microflora at the skin surface, especially those responsible for the development of body odor, antiperspirant actives, whose function is to reduce or eliminate the appearance of perspiration at the skin surface, and anticholinergic actives, whose function is to reduce or eliminate the generation of perspiration before it reaches the skin surface.

In the following examples standardized pectinate is used as designation for the pectin according to this invention.

"Standardized calcium pectinate" means the calcium salt obtained according to the present invention and standardized with sugar or other inert materials to obtain uniform performance.

EXAMPLE 1

Pate with Reduced Fat Content

Liver pate as produced traditionally contains up to 75% fat. The fat in the formulation is necessary to give the pate the desired form stability and mouth feel; without fat, the pate will be very dry.

It has surprisingly been found that the addition of dry calcium pectinate of this invention makes it possible to prepare a pate with less than 5% fat using the formulation below:

| Ingredients | Full Fat % | Low Fat % |
|---|---|---|
| Liver | 24.00 | 24.00 |
| Pork meat 1 | 12.00 | 12.00 |
| Beef 1 | 20.00 | 20.00 |
| Animal fat | 20.00 | — |
| Water | 17.48 | 40.80 |
| Salt | 1.70 | 1.30 |
| Powdered Onion | 0.42 | — |
| Caseinate | 1.00 | — |
| Ascorbate | 0.05 | 0.05 |
| Wheat flour | 2.50 | — |
| Potato flour | 0.50 | — |
| Flavor | — | 1.00 |
| Phosphate | 0.20 | — |
| Pepper | 0.15 | — |
| Genugel carrageenan type MG-11 | — | 0.35 |
| Standardized calcium pectinate | — | 1.0 |
| Total | 100.00 | 100.0 |

Process:
1. Liver is ground with salt for 3 minutes.
2. Pork meat is added and ground for 3 minutes.
3. Dry ingredients are added.
4. Water is added and grinding continued for 3 minutes until homogeneous.
5. Finally the beef is ground to desired consistency.
6. The ground meat is poured into cans and autoclaved at 115° C. for 60 minutes.

The pate obtained is judged by specialists in the field to have the same texture as the traditional pates and to be as juicy and tasteful. The composition and process in only an example. Those skilled in the art will be able to modify the composition and the process to suit their special taste preferences and process conditions.

EXAMPLE 2

Thousand Island Dressing with 3% Oil

A thousand island dressing with only 3% oil can be produced with the same organoleptic impression as experienced with the full fat version according to the formulation below.

| Order of Addition | Ingredients | % |
|---|---|---|
| A | Oil | 3.0 |
|   | Standardized calcium pectinate | 0.3 |
|   | Whey protein concentration./Na-caseinate | 1.0 |
| B | Water | 48.75 |
|   | Egg yolk (past. 1.2% salt) | 5.0 |
|   | Modified starch | 1.0 |
|   | Skimmed milk powder | 4.0 |
|   | Sodium benzoate (20% solution.) | 0.5 |
|   | Potassium sorbate (20% solution.) | 0.5 |
|   | Sugar | 12.0 |
|   | White pepper | 0.05 |
|   | Paprika | 0.1 |
|   | Garlic powder | 0.1 |
|   | Fat replacer flavor | 0.2 |
| C | Tarragon vinegar (7% acid) | 5.0 |
|   | Vinegar neutral (5%) | 5.0 |
|   | Tomato Paste | 6.5 |
|   | Salt | 1.5 |
|   | Acidified chopped cucumbers | 3.0 |
|   | Pickles | 2.5 |
| Total |   | 100.0 |

Ingredient note:

Whey protein concentration: PSE 73 from Denmark Protein

Skimmed milk Powder: Super Instant

Modified starch: C-top 12616 from Cerestar

Fat replace flavor: Flav-O-lok 610486 from Tastemaker, Holland

Process:
1. Mix Ingredients (A).
2. Mix egg yolk+skimmed milk powder into water phase and add perservatives. Blend dry ingredients (B) and mix into water phase. Hydrate for 5 minutes.
3. Mix (A) and (B) and pour into processing equipment (Kuruma or Stephan mixer or equivalent). Mix until homogeneous.
4. Mix ingredients (C) and add slowly. Process until homogeneous, smooth product is achieved.
5. Fill into preferred packaging.

EXAMPLE 4

Mortadella Sausage was prepared with the following composition:

| Ingredients | % |
|---|---|
| Turkey scraps | 45.0 |
| Sodium tripolyphosphate | 0.5 |
| Nitrate salt | 1.6 |
| Genugel type MB-73 | 0.5 |
| Soy isolate | 1.0 |
| Spices | 0.56 |
| Standardized calcium pectinate | 0.9 |
| Ice/water | 46.89 |
| Potato starch | 3.0 |
| Sodium ascorbate | 0.05 |
| Total Ingredients | 100.0 |

Process for preparing Mortadella with Standarized Calcium Pectinate

1. Add 80% of the meat to a bowl chopper and start cutting at low speed.
2. Add phosphate.
3. Add nitrite salt.
4. Add half the water/ice.
5. Add Standardized calcium pectinate.
6. Add Genugei® type MB-73, soy isolate and spices.
7. Add remaining water/ice.
8. Add remaining meat quantity.
9. Add potato starch.
10. Cut until desired consistency and texture are achieved.

Smokehouse program

1. Fill the meat into 50 mm smoke permeable casings.
2. Dry the sausages for 30 minutes at 50° C. Smoke for 1½ hours at 55° C. (20% air humidity). Cook at 75° C. until the core temperature reaches 72° C. Cool immediately.

EXAMPLE 4

A mayonnaise with only 3% oil and the same eating impression as a full fat mayonnaise can be prepared in a very easy way.

| | Ingredients | % |
|---|---|---|
| A | Water | 30.0 |
| | Soy oil | 3.0 |
| | Egg yolk | 4.0 |
| | Modified starch | 3.0 |
| B | Water | 44.15 |
| | Sodium benzoate 20% solids w/v | 0.3 |
| | Potassium sorbate 20% solids w/v | 0.2 |
| C | Standardized calcium pectinate | 1.0 |
| | Stabilizer (Hercofood ET 015-1) | 0.6 |
| | Sugar | 5.0 |
| D | Salt (NaCl) | 1.2 |
| E | Vinegar (9.6%) | 5.0 |
| | Mustard | 0.05 |
| | Total | 100.0 |

Process:

1. Add egg yolk, oil and water (A) to Stephan mixer and mix until homogeneous appearance. Add starch and mix again until homogeneous appearance.
2. Add preservative and water (B), mix again.
3. Mix the dry ingredients (C), add to the other ingredients in the mixer, mix for 5 minutes. Let the solution rest for 10 minutes.

The eating quality can be changed from rather thin to heavy by varying the concentration of Standardized calcium pectinate. The process is easy—only a blender or a colloid mill is necessary and no homogenizer or other expensive equipment is needed.

EXAMPLE 5

Low Fat Ice Cream

Ice cream normally contains 8–12% milk fat or more to give a rich mouth feel. It has been shown that the same eating quality can be obtained preparing an ice cream with Standardized calcium pectinate and only 1.5% fat.

| | Ingredients | % |
|---|---|---|
| A | Milk with 1.5% fat | 78.00 |
| B | Sugar | 15.00 |
| | Skimmed milk powder | 6.60 |
| | Standardized calcium pectinate | 0.56 |
| | Emulsifier/stabilizer | 0.80 |
| | (Hercofood II 30E-1) | |
| | Vanilla flavor | 0.04 |
| | Total | 100.00 |

Process:

1. Weigh out the milk (A).
2. Mix all dry ingredients (B).
3. Disperse the dry powder into the milk.
4. Heat to 80° C.
5. Cool to 5° C.
6. Let the ice-mix ripen for a minimum of 2 hours or until the following day.
7. Freeze the ice-mix, using an ice machine and then in a deep freezer.

The process is simplified compared with traditional ice cream manufacturing procedures. Homogenization is not necessary.

The dry ingredients can be used as a ready blend to mix with semi-skimmed milk by the housewife or ice cream manufacturer.

EXAMPLE 6

Low Fat Mayonaise 20% Oil

| Order of Addition | Ingredients | % |
|---|---|---|
| A | Water | 56.2 |
| | Egg yolk | 4.0 |
| | Sodium benzoate | 0.3 |
| | (20% solution. w/v) | |
| | Potassium sorbate | 0.2 |
| | (20% solution) | |
| B | Soy oil | 20.0 |
| | Standardized calcium pectinate | 0.6 |
| | Sugar | 5.0 |
| | VPC 8080 | 2.0 |
| | Modified starch | 3.0 |
| C | Vinegar estragon (7%) | 7.0 |
| | Mustard (Dijon) | 0.5 |

-continued

| Order of Addition | Ingredients | % |
|---|---|---|
| | Salt (NaCl) | 1.2 |
| | Total | 100.0 |

Process:
1. Mix water, egg yolk and preservatives.
2. Mix (B) carefully with oil and pour into Stephan mixer.
3. Add (A) to (B) and mix for 5 min.
4. Add (C) and mix for 5 min.
5. Cool to 5° C. (quickly)

Note: may be prepared without egg yolk (with added color, increasing the Standardized calcium pectinate.)

EXAMPLE 7

Deep-Frozen Low Fat Sauces

Freeze/thaw stable sauces with standardized calcium pectinate was prepared with the following composition:

| Ingredients | % |
|---|---|
| Water | 83.48 |
| Agar 900-A1 | 1.00 |
| Standardized calcium pectinate | 0.40 |
| Starch C top | 4.00 |
| Skim milk powder | 1.40 |
| Sodium caseinate | 1.50 |
| Salt | 1.00 |
| Pepper | 0.02 |
| Flavor | 0.20 |
| Cream | 7.00 |
| Total | 100.00 |

Process:
1. Mix dry ingredients and add to water and cream using a high speed mixer (Silverson)
2. Bring to the boil while stirring.
3. Pour into molds and cool to 5° C.
4. Cut into cubes and freeze.

EXAMPLE 8

Low Fat Imitation Sour Cream

| Order of Addition | Ingredients | % |
|---|---|---|
| A | Hardened palm kernel oil (melting point 35° C.) | 3.0 |
| | Distilled monoglycerides | 0.3 |
| | Lactic acid ester monoglycerides | 0.45 |
| B | Skimmed milk powder | 4.0 |
| | Maltodextrine (dextrose equivalent 10–12) | 10.0 |
| | Standardized calcium pectinate | 0.6 |
| | Genu Carrageenan LRA-50 | 0.8 |
| C | Skimmed milk | 80.85 |
| | Total Ingredients | 100.00 |

Ingredient note:
Distilled monoglyceride, e.g., Palsgaard 0291.
Lactic acid ester of monoglycerides, e.g., Palsgaard 0404.

Process:
1. Melt fat and emulsifier (A) and heat to 80° C.
2. Mix dry ingredients (B) and dissolve in water phase (C) at 35° C. under continuous agitation. Heat to 80° C.
3. Mix oil phase into water phase under high speed mixing and mix at 75–80° C. for 30 minutes.
4. Homogenize at 150 bars at 75° C.
5. Adjust pH to 4.0 (e.g., with a lactic acid solution).
6. Cool under agitation to approximately 20–30° C.
7. Fill.
8. Ageing at 5° C. for 48 hours.

EXAMPLE 9

Low Fat Spread with 40% Fat with Standardized CSP

Traditional yellow spreads hold up 80% fat, but with the use of Standardized calcuim pectinate it is possible to make a low fat spread of high quality with a fat content of 40% only.

| Order of Addition | Ingredients | % |
|---|---|---|
| A | Coconut oil (Kokoneutrex)[1] | 2.5 |
| | Hydrogenated palm oil (Palmowar EE42)[2] | 9.3 |
| | Soya oil (Shogun) | 27.7 |
| B | Distilled monoglyceride (Palsgaard 0291)[3] | 0.6 |
| C | Standardized calcium pectinate | 0.8 |
| | Water | 58.1 |
| | Salt | 1.0 |
| | Aroma, color, vitamins, preservatives | optional |
| | Total Ingredients | 100.0 |

[1]Melting point 26° C.
[2]Melting point 42° C.
[3]Distilled monoglyceride

Process:
1. Heat the oil phase (A) to 43–45° C.
2. Melt the emulsifier (B) with 5 parts of oil/fat from (A) by heating to 60° C. and add to the remaining oil/fat.
3. Heat the water phase (C) to 43–45° C.
4. Prepare a water in oil emulsion by mixing the water phase in the oil phase.
5. Process the emulsion in a tube chiller, working unit and tube chiller (combinator from Schroder, Germany).

Comments:
The Low Fat Spread produced with Standardized calcium pectinate according to the above example is more glossy and smoother than the corresponding margarines on the market, and it has an excellent melt down and coherent texture.

The combinator was run under the following conditions:

| | |
|---|---|
| Inlet temperature | 43–45° C. |
| Outlet temperature CC1 (tube chiller No. 1) | 23–25° C. |
| A1 (working unit) | 35–40° C. |
| CC2 (tube chiller No. 2) | 15–25° C. | rpm of CCA: 800; A1: 1400, CC2: 750

EXAMPLE 11

Low Fat Spread with 20–25% Fat with Standardized Calcium Pectinate

Traditional yellow spreads hold up to 40–80% fat, but with the use of Standardized calcium pectinate it is possible to make a low fat spread of high quality with a fat content of 20–25% only. Which one of the two below recipes to be chosen depends on the preferred emulsifier system.

| Order of Addition | Ingredients | 20% fat | 25% % |
|---|---|---|---|
| A | Hydrogenated palm oil (Palmowar EE42)[(1)] | 6.6 | 8.3 |
|   | Soya oil (Shogun) | 13.4 | 16.2 |
| B | Emulsifier |  |  |
|   | (Palsgaard 0291)[(2)] | 0.7 | — |
|   | (Palsgaard 4110)[(3)] | 0.2 | — |
|   | (Palsgaard 0094)[(2)] | — | 1.0 |
| C | Standardized calcium pectinate | 0.8 | 0.8 |
|   | Water | 77.3 | 72.7 |
|   | Salt | 1.0 | 1.0 |
|   | Aroma, color, vitamins, preservatives | optional | optional |
|   | Total Ingredients | 100.0 | 100.0 |

[(1)]Melting point 42° C.
[(2)]Distilled monoglyceride
[(3)]Polyglycerol polyricinoleate Process:
1. Heat the oil phase (A) to 43–45° C.
2. Melt the emulsifier (B) with 5 parts of oil/fat from (A) by heating to 60° C. and add to the remaining oil/fat.
3. Heat the water phase (C) to 43–45° C.
4. Prepare a water in oil emulsion by mixing the water phase in the oil phase.
5. Process the emulsion in a tube chiller, working unit and tube chiller (combinator from Schroder, Germany).

Comments:
The Low Fat Spread produced with Standardized calcium pectinate according to the above example is more glossy and smoother than the corresponding margarines on the market, and it has an excellent melt down and coherent texture.

The combinator was run under the following conditions:

| Inlet temperature | 43–45° C. |
|---|---|
| Outlet temperature CC1 (tube chiller No. 1) | 23–25° C. |
| A1 (working unit) | 35–40° C. |
| CC2 (tube chiller No. 2) | 15–25° C. | rpm of CCA: 800; A1: 1400, CC2: 750

EXAMPLE 11

Skimmed Milk with Improved Mouthfeel

| Ingredients | % |
|---|---|
| Standardized calcium pectinate | 0.30 |
| Stabilizer GENULACTA carrageenan type LK-60 | 0.03 |
| Flavor* | 0.05 |
| Skimmed milk | 99.62 |
| Total | 100.0 |

*Tastemaker 630214E

Process:
1. Dry mix all the ingredients.
2. Disperse the dry mix into the cold milk by use of a high speed mixer.
3. Homogenize at 200 bar, 1 step.
4. Pasteurize at 85° C.
5. Fill at 18–20° C.
6. Store at 5° C.

EXAMPLE 12

A purified pectin extract as obtained from a commercial production of pectin was adjusted to pH 4 and mixed with a solution of $CaCl_2$ in 80% isopropyl alcohol in the proportion of 10% isopropyl alcohol and 90% of pectin extract.

After mixing, gel particles visable to the naked eye were formed and the mixture contained 45 mM calcium ion and 8% isopropyl alcohol. Additional alcohol was then added to complete precipitation and the mixture was filtered. The precipitate was washed and then dried at a temperature of 65° C. for about 16 hours. The dried material was then milled and sleved to a particle size of less than 250 micrometers.

This material was then tested for swollen particle size by suspending in distilled water and the swollen particles were then examined microscopically. The particles were observed to have a mean equivalent diameter of greater than 100 micrometers.

What is claimed is:

1. A composition comprising a dry, heat stable, pectinate, which when suspended in distilled water, swells to heat stable particles, more than 90% of which particles have an equivalent diameter greater than 200 micrometers, and wherein the pectinate comprises a cation salt of pectin where the cation is selected from a metal ion derived from salts selected from the group consisting of alkaline earth metal salts, alkali metal salts, transition metal salts, and mixtures thereof.

2. The composition of claim 1, wherein the equivalent diameter is at least 300 micrometers.

3. The composition of claim 2, wherein the equivalent diameter is at least 400 micrometers.

4. The composition of claim 1, wherein more than 95% of the particles have an equivalent diameter greater than 200 micrometers.

5. The composition of claim 1, wherein the cation is selected from the group consisting of calcium, magnesium, iron, zinc, potassium, sodium, aluminum, manganese, and mixtures thereof, with the proviso that when at least one of potassium or sodium is used, at least one of calcium, magnesium, iron, zinc, aluminum, or manganese is also used.

6. The composition of claim 5, wherein the salts are selected from the group consisting of salts of calcium, magnesium, zinc, iron, and mixtures thereof.

7. The composition of claim 6, wherein the cation is calcium.

8. A process for making the pectinate of claim 1 comprising
   a) converting a pectin starting material into a pectinate in a liquid medium,
   b) drying the pectinate, and
   c) selecting conditions in a) and/or b) such as to allow for the production of dry pectinate which, when suspended in distilled water, will swell to heat stable particles, more than 90% of which particles have an equivalent diameter greater than 200 micrometers.

9. The process of claim 8 wherein a) is performed under substantially non-shear conditions.

10. The composition comprising a dry, heat stable, pectinate, which when suspended in distilled water, swells to heat stable particles, which particles have a mean equivalent diameter of greater than 200 micrometers at a magnification of 20–40×.

11. The composition of claim 10, wherein the mean equivalent diameter is greater than 300 micrometers.

12. The composition of claim 11, wherein the mean equivalent diameter is greater than 400 micrometers.

13. A composition comprising a dry, heat stable, pectinate, which when suspended in distilled water, swells to heat stable particles, more than 90% of which particles have an equivalent diameter greater than 200 micrometers at a magnification of 20–40×, and wherein the pectinate comprises a cation salt of pectin where the cation is selected from a metal ion derived from salts. selected from the group consisting of alkaline earth metal salts, alkali metal salts, transition metal salts, and mixtures thereof.

14. The composition of claim 13, wherein the equivalent diameter is at least 300 micrometers.

15. The composition of claim 14, wherein the equivalent diameter is least 400 micrometers.

16. The composition of claim 13, wherein more than 95% of the particles have an equivalent diameter greater than 200 micrometers.

17. The composition of claim 13, wherein the cation is selected from the group consisting of calcium, magnesium, iron, zinc, potassium, sodium, aluminum, manganese, and mixtures thereof, with the proviso that when at least one of potassium or sodium is used, at least one of calcium, magnesium, iron, zinc, aluminum, or manganese is also used.

18. The composition of claim 17, wherein the salts are selected from the group consisting of salts of calcium, magnesium, zinc, iron, and mixtures thereof.

19. The composition of claim 18, wherein the cation is calcium.

20. A process for making the pectinate of claim 13 comprising:
    a) converting a pectin starting material into a pectinate in a liquid medium,
    b) drying the pectinate, and
    c) selecting conditions in a) and/or b) such as to allow for the production of dry pectinate which, when suspended in distilled water, will swell to heat stable particles, more than 90% of which particles have an equivalent diameter greater than 200 micrometers at a magnification of 20–40×.

21. The process of claim 20 wherein a) is performed under substantially non-shear conditions.

* * * * *

Disclaimer

6,207, 194—Poul-Egede Glahn, Skensved (DK). PECTIN PROCESS AND COMPOSITION. Patent dated March 27, 2001. Disclaimer filed May 8, 2002, by the assignee, Hercules Incorporated.

The term of this patent shall not extend beyond the expiration date of Pat. No. 6,159,503.
*(Official Gazette, June 10, 2003)*